United States Patent [19]

Poxleitner et al.

[11] Patent Number: 5,268,711
[45] Date of Patent: Dec. 7, 1993

[54] OPHTHALMOSCOPE

[75] Inventors: Martin Poxleitner, Königsbronn; Gerhard Gaida, Aalen, both of Fed. Rep. of Germany

[73] Assignee: Carl-Zeiss-Stiftung, Heidenheim, Fed. Rep. of Germany

[21] Appl. No.: 823,250

[22] Filed: Jan. 21, 1992

[30] Foreign Application Priority Data

Jan. 18, 1991 [DE] Fed. Rep. of Germany ....... 4101356

[51] Int. Cl.$^5$ ................................................ A61B 3/10
[52] U.S. Cl. ..................... 351/214; 351/205; 351/221
[58] Field of Search ................ 351/205, 214, 221

[56] References Cited

U.S. PATENT DOCUMENTS 4,765,730  8/1988  Webb .
4,886,351 12/1989  Sabban et al. .

FOREIGN PATENT DOCUMENTS 0145563  7/1985  European Pat. Off. .
0223356  5/1987  European Pat. Off. .
8912757  1/1990  Fed. Rep. of Germany .
90/00025 1/1990  PCT Int'l Appl. ................ 351/221

OTHER PUBLICATIONS

"Fundamentals of Optics" by Francis A. Jenkins and Harvey E. White, Mc-Graw-Hill, 1950, pp. 91 and 92.

Primary Examiner—Bruce Y. Arnold
Assistant Examiner—Hung Xuan Dang
Attorney, Agent, or Firm—Walter Ottesen

[57] ABSTRACT

The invention is directed to an ophthalmoscope and especially a confocal raster ophthalmoscope wherein the scanning unit can be imaged on the pupil of the eye with different imaging scales. The switchover between the imaging scales is realized by a displacement of a spherical concave mirror of the ophthalmoscope. The astigmatism of the concave mirror is changed because of the changed imaging scale and is compensated in that the displacement of the concave mirror has a displacement component perpendicular to the main axis of this mirror.

21 Claims, 3 Drawing Sheets

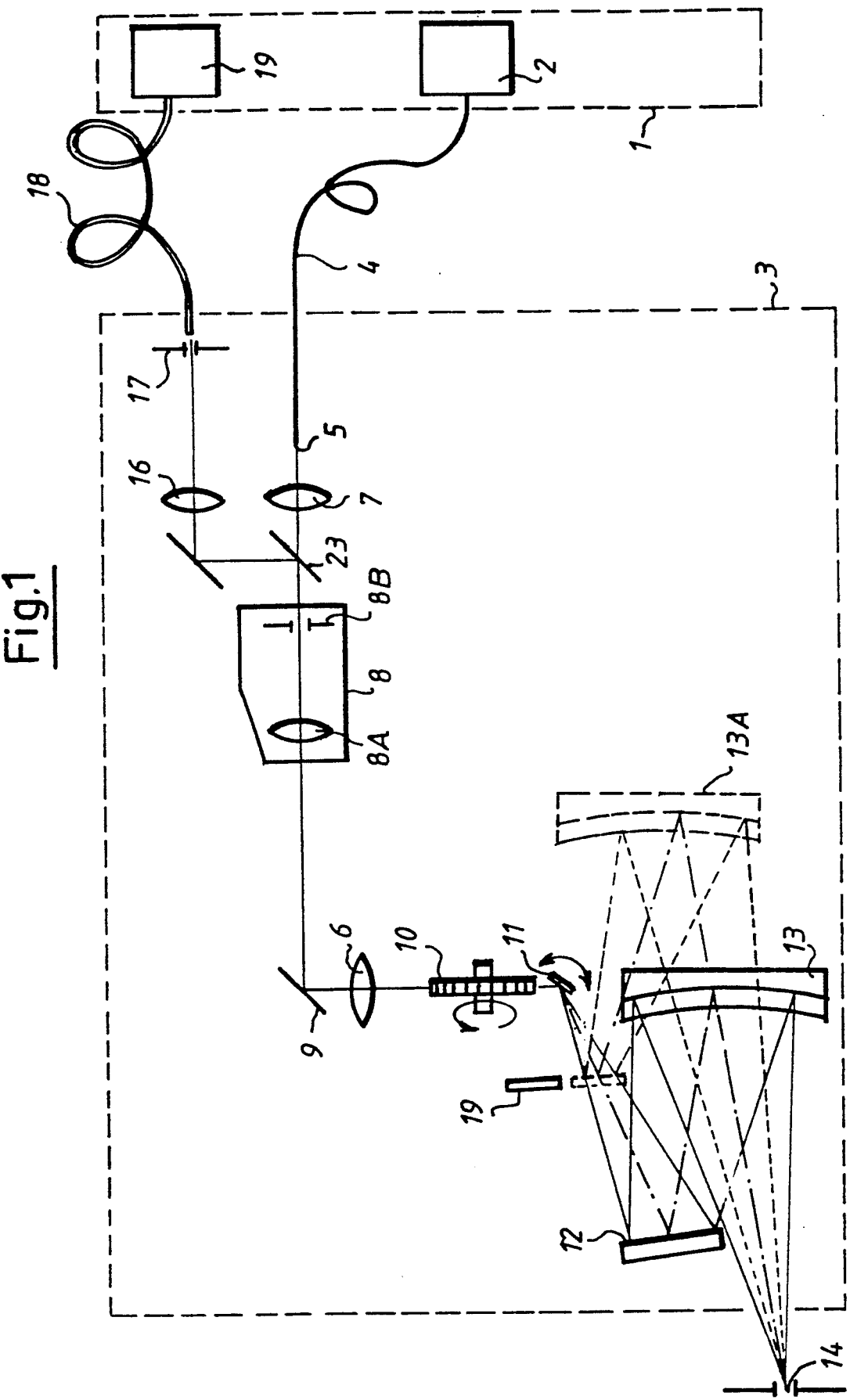

OPHTHALMOSCOPE

FIELD OF THE INVENTION

The invention relates to an ophthalmoscope having a scanning unit and a spherical concave mirror which images the scanning unit on the eye of a patient and is switchable into at least two different positions.

BACKGROUND OF THE INVENTION

Such an ophthalmoscope is known from U.S. Pat. No. 4,765,730 and operates to scan the ocular fundus with high resolution. For this purpose, the light of a laser is deflected in two mutually perpendicular directions and is imaged on the eye of the patient. The light reflected at the ocular fundus transilluminates the same scanning unit in the opposite direction and is thereafter directed into a viewing beam path.

The scanning unit comprises two elements which scan the incident light beam in two mutually perpendicular directions. An imaging optic for compensating for astigmatism of the tilted concave mirror is provided between the two elements.

A telescope having a magnification different than 1x is provided between the concave mirror and the ocular fundus for changing the scanning region and thereby for changing the field of view. By exchanging the telescope lenses, it is then possible to switch the magnification over to the inverse value.

However, such a telescope, on the one hand, causes additional reflections at the telescope lenses which reduce the contrast of the viewed image. On the other hand, the additional components make the overall ophthalmoscope more expensive and the telescope furthermore increases that apparatus part of the ophthalmoscope which is to be aligned onto the eye of the patient.

U.S. Pat. No. 4,765,730 suggests an alternate possibility for changing the field of view. This possibility provides that the concave mirror is brought into a second position so that the scanning unit is imaged with another imaging scale on the eye of the patient. However, no information is provided as to what characteristics the switching positions should have or how the switchover between the switching positions should take place. In lieu thereof, it is stated that this alternative is difficult to realize.

SUMMARY OF THE INVENTION

It is an object of the invention to provide an ophthalmoscope of the kind mentioned above wherein the scanned region and therefore the field of view can be varied. It is another object of the invention to provide an ophthalmoscope of this kind wherein the scanned region and field of view can be varied inexpensively while at the same time providing the most compact configuration possible for the apparatus part which is to be aligned onto the eye of the patient.

According to a feature of the invention, the optical path lengths between the scanning unit and the concave mirror are different in the different switching positions and the main axis of the concave mirror extends along lines which are parallel to each other in the different switching positions.

The possibility for switching over the field of view is described in U.S. Pat. No. 4,765,730 as being difficult. However, it is precisely this possibility of switching over the field of view which the applicants' invention recognizes as being especially advantageous when configured pursuant to the applicants' invention. The basis of the applicants' invention is the recognition that it is possible to bring the concave mirror in such displaced positions that this mirror images the scanning unit with different imaging scales and that the astigmatism of the concave mirror in the two switching positions can have the same value in that the concave mirror is displaced perpendicularly to its main axis. An additional tilting of the concave mirror between both switching positions is not necessary. In this way, the concave mirror can be brought into different switching positions in an especially simple manner by means of a single-dimension linear displacement. Corresponding guide elements can be provided for this linear displacement.

A belt drive can be provided for the displacement which is driven by an electric motor and the concave mirror is displaced therewith.

The field of view switchover according to the invention is especially advantageous to utilize when the scanning unit comprises two elements which are arranged one behind the other in the direction of the light path and when the scanning movements are carried out in mutually perpendicular directions. These elements are arranged in the tangential and sagittal foci of the concave mirror. The astigmatism of the concave mirror which likewise changes with a change of the imaging scale is compensated by the displacement of the concave mirror perpendicularly to the main axis. A change of displacement between both scanning elements is not necessary so that the scanning elements can be fixedly mounted in an apparatus part.

An element of the scanning unit is preferably a polygon-mirror scanner having a scanning frequency corresponding to the line frequency of a monitor. The monitor displays an image of the ocular fundus in the form a dot matrix.

Any desired number of intermediate values of the imaging scale between a smallest and a largest value are possible in principle by displacing the concave mirror with these limit values being determined by the mechanical stops of the displacement path. However, it is especially simple and advantageous when only two different imaging scales can be adjusted. Then the condition can be achieved that the imaging unit is imaged on the same imaging point in both switching positions by means of a simple switching mirror which can be switched into and out of the beam path.

According to another feature of the invention, the ophthalmoscope is preferably configured as a confocal ophthalmoscope. A point light source is then provided which emits light with which the ocular fundus can be scanned. A pinhole diaphragm is provided at the viewing end in a plane conjugated to the point light source. The scanning unit is mounted on a common region of the illuminating beam path and the viewing beam path.

Preferably, an arrangement for compensating for the ametropia of the eye of the patient is provided in the common region of the illuminating and viewing beam path. Independently of the selected imaging scale, the light beams can be made to impinge on the pupil of the eye with the same convergence with the aid of the above compensating unit by means of a control.

According to another feature of the invention, that apparatus part which is to be aligned to the eye of the patient can be configured so as to be especially compact and therefore also convenient to operate.

BRIEF DESCRIPTION OF THE DRAWINGS

The invention will now be described with reference to the drawings wherein:

FIG. 1 is a schematic of the ophthalmoscope according to the invention;

DESCRIPTION OF THE PREFERRED EMBODIMENTS OF THE INVENTION

Figure 2A:
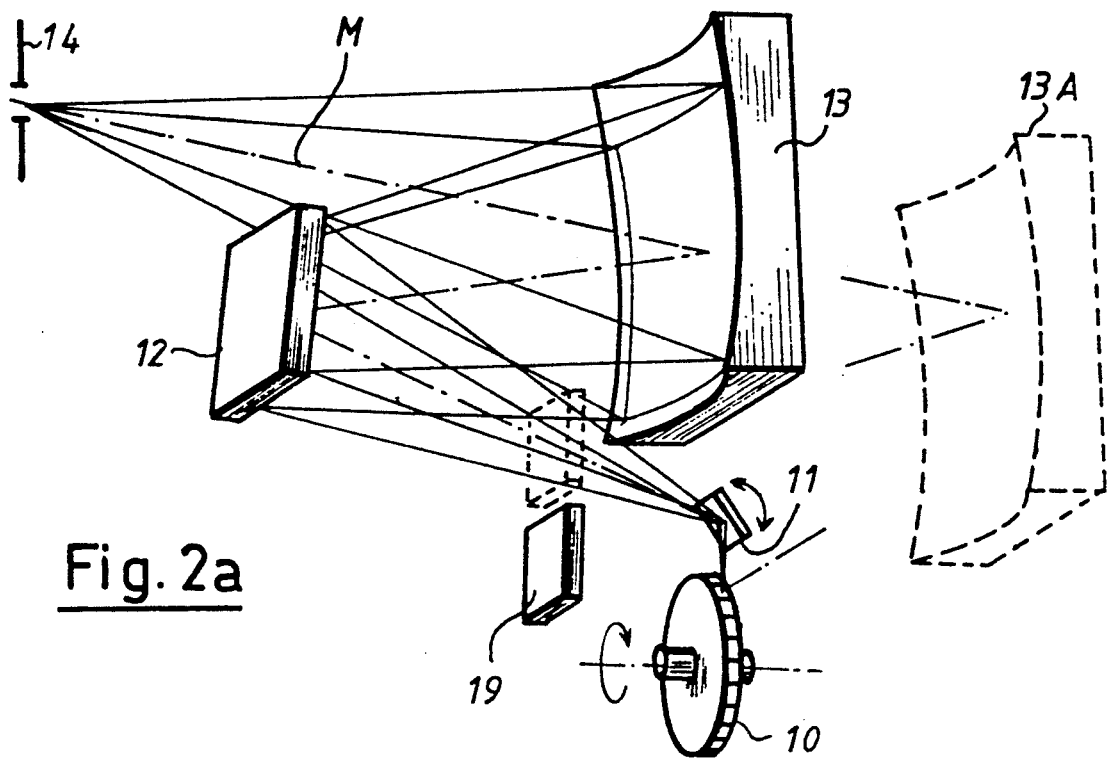
FIG. 2a is a first perspective view of the part of the ophthalmoscope of FIG. 1 facing toward the patient in a first switching position of the concave mirror.

The ophthalmoscope of FIG. 1 comprises a supply unit 1 and an apparatus upper part 3 which is movable relative to the supply unit 1 and which is to be aligned on the eye of the patient. The light of a laser 2 mounted in the supply unit 1 is guided via a light-wave conductor 4 into the upper part 3. The end face 5 of the light-wave conductor 4 defines a point light source. An objective 7 is provided downstream of the light source and collects the light therefrom. For this purpose, the end face 5 of the light-wave conductor 4 is mounted in the focal point of the objective 7. A compensating unit 8 is arranged behind the objective 7 for compensating for the ametropia of the eye of the patient. This compensating unit is comprised essentially of a lens 8A and a diaphragm 8B and is disclosed in U.S. Pat. No. 4,886,351 incorporated herein by reference.

A deflecting mirror 9 is mounted behind the compensating unit 8 and deflects the beam path via a further objective 6 to a scanning unit. The scanning unit comprises a polygon mirror scanner 10 which deflects the light beam perpendicularly to the plane of the drawing and a galvanometer scanner 11 which deflects the light beam in the plane of the drawing. A spherical concave mirror 13 images the scanning unit onto the pupil 14 of the eye of the patient via a deflecting mirror 12 arranged upstream of the concave mirror 13. The convergence of the incident light rays is adjusted with the aid of the compensating unit 8 in such a manner that the lens of the eye of the patient focuses the incident light rays on the ocular fundus.

The spherical concave mirror 13 collects the light reflected back from the ocular fundus and mirrors this light via the deflecting mirror 12 and the scanning unit (10, 11) back to the compensating unit 8. A partially transmittent mirror 23 is disposed behind the compensating unit 8 and deflects the back-reflected light into the viewing beam path. A third objective 16 is mounted in this viewing beam path and focuses the back-reflected light into the plane of a pinhole diaphragm 17. The pinhole diaphragm 17 is mounted in a plane confocal to the plane of the end face 5 and confocal to the plane of the ocular fundus. The diameter of this confocal diaphragm 17 is selected so that only that light of the laser focus generated by the lens of the eye (that is, that light which is reflected at the ocular fundus) is transmitted through the pinhole diaphragm 17. The light scattered or reflected before or after the laser focus is, in contrast, absorbed by the pinhole diaphragm 17. In this way, by means of the pinhole diaphragm 17, an improvement of the contrast and of the resolution is achieved. A second flexible light conductor 18 is provided behind the pinhole diaphragm 17 which conducts the light transmitted through the pinhole diaphragm 17 to a photomultiplier mounted in the supply unit 1.

The scanning angle is that angle at which the light rays impinge upon the pupil 14. For switching over the imaging scale or the scanning angle, a switching position shown in phantom outline is provided for the concave mirror 13 and wherein the concave mirror is identified by reference character 13A. A switching mirror 19 is switched into the beam path between the scanning unit and the deflecting mirror 12 simultaneously with the switching of the concave mirror into the second position so that this switching mirror 19 deflects the scanning beam onto the spherical concave mirror 13A. In the second switching position, the optical path between the scanning unit and the spherical concave mirror 13A is shorter than the optical path between the scanning unit and the concave mirror 13 in the first switching position. Therefore, in the second switching position, the concave mirror 13A images the scanning unit at a lower imaging scale onto the pupil 14 than in the first switching position. Here, it is important that the concave mirror (13, 13A) images the scanning unit on the same pupil 14 in both switching positions. The apparatus upper part 3 therefore does not have to be again aligned onto the eye of the patient after a switchover of the field of view is made.

In synchronism with the switchover of the concave mirror (13, 13A), the lens 8A is so displaced in the compensating unit 8 that the convergence or divergence of the light beam incident on the pupil 14 is independent of the switching position of the concave mirror (13, 13A). For this purpose, the drive for the concave mirror (13, 13A) is coupled to the drive for the lens 8A. The ocular fundus of the patient is then always in a plane conjugated to the end face 5 of the light-wave conductor 4. Likewise, the end face 5 of the light-wave conductor 4 and the pinhole diaphragm 17 are always mounted in mutually conjugated planes.

Figure 3:
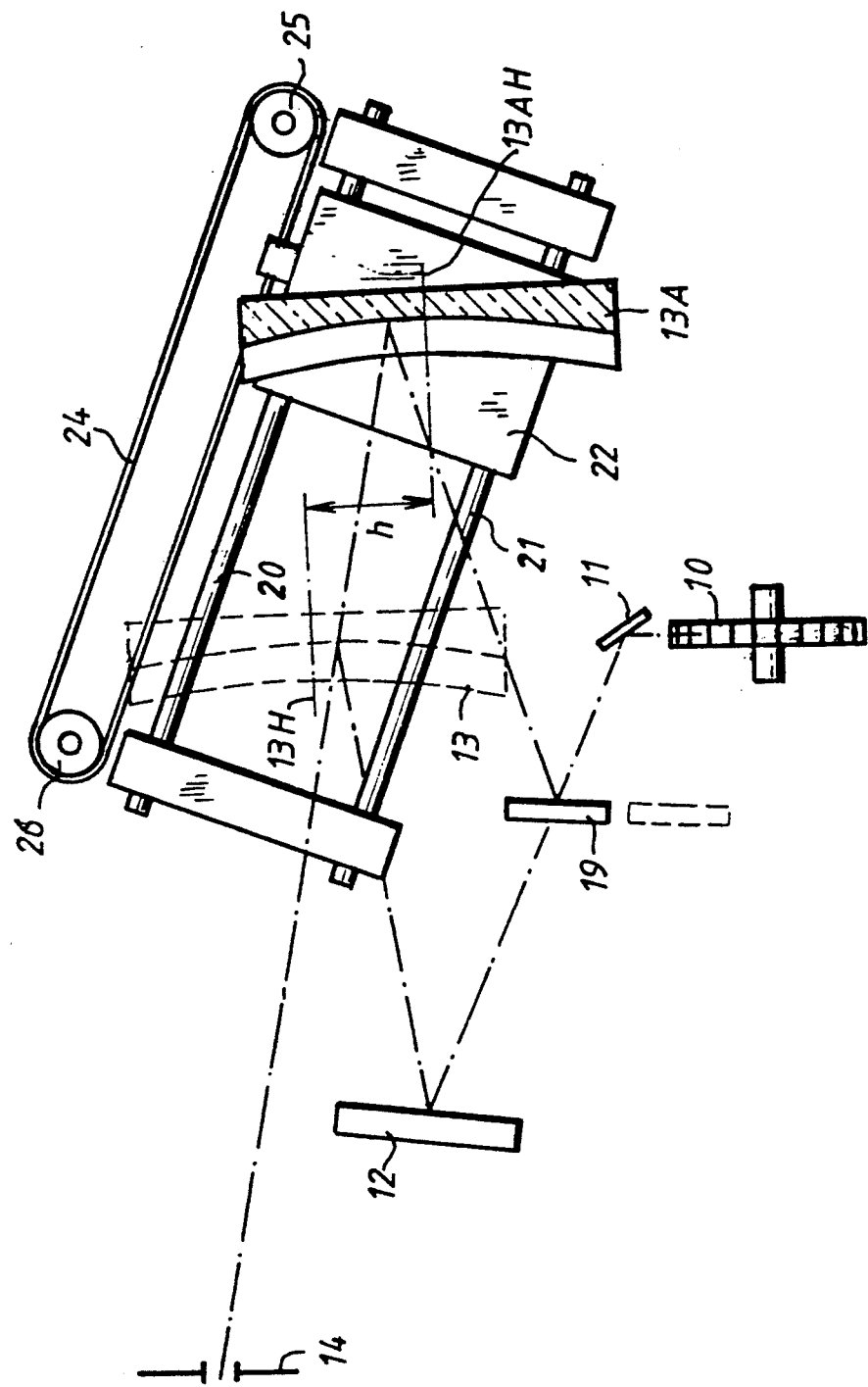

The switchover of the concave mirror 13 takes place as shown in FIG. 3 by a linear displacement of the mirror with the displacement having a displacement component parallel to the main axis (13H, 13AH) as well as a displacement component perpendicular to the main axis (13H, 13AH) of the concave mirror (13, 13A). The individual components are provided with the same reference characters in FIG. 3 as they are in FIG. 1. The mirror 13A is mounted on a carrier 22 which is motorically displaceable along two guide rails (20, 21). A belt drive is provided for the motoric displacement wherein a toothed belt 24 is guided over a driven wheel 25 mounted on a motor shaft and a follower wheel 26. The mirror carrier 22 is attached to the toothed belt 24 and is entrained by the belt. The displacement along the guide rails (20, 21) takes place in that the main axis 13AH of the concave mirror is displaced into the second switching position by an amount (h) perpendicular to the main axis 13H. The imaging scale with which the scanning unit (10, 11) is imaged into the plane of the pupil 14 is provided by the optical path length between the scanning unit and the spherical concave mirror (13, 13A) in the particular switching position. The astigmatism of the concave mirror (13, 13A) is changed by two effects by the displacement thereof. The first effect is a change of the astigmatism which is caused by the changed imaging scale. The second effect is a change of the astigmatism based on different angles at which the light impinges on the concave mirror (13, 13A) in the two switching positions. The reason for this is that the mirror 12 and the switching mirror 19 are not aligned parallel to each other. The spacing (h), by which the spherical concave mirror (13, 13A) is displaced perpendicularly to its main axis (13H, 13AH) when switching, is precisely so selected that in both switching positions, the astigmatism of the concave mirror (13, 13A) is the same. The polygon mirror scanner 10 is then mounted in the sagittal focus and the galvanometer scanner 11 is mounted in the tangential focus of the concave mirror (13, 13A). Both elements (10, 11) of the scanning unit are therefore imaged sharply in the plane of the pupil 14 in both switching positions.

The formulas for calculating the positions of the tangential and sagittal foci of a tilted concave mirror are, for example, described in the reference text of Jenkins et al entitled "Fundamentals of Optics", Mc Graw-Hill, 1950, page 92. The required spacing (h) as well as the position and the orientation of the switching mirror 19 can be clearly defined with the aid of geometric considerations based on these formulas and the following requirements: that the pupil 14 is at the same position in both switching positions; the elements (10, 11) of the scanning unit are mounted at the same locations in both switching positions; and, the scales with which the concave mirror (13, 13A) images the two elements (10, 11) of the scanning unit on the pupil 14 are precisely given.

Figure 2B:
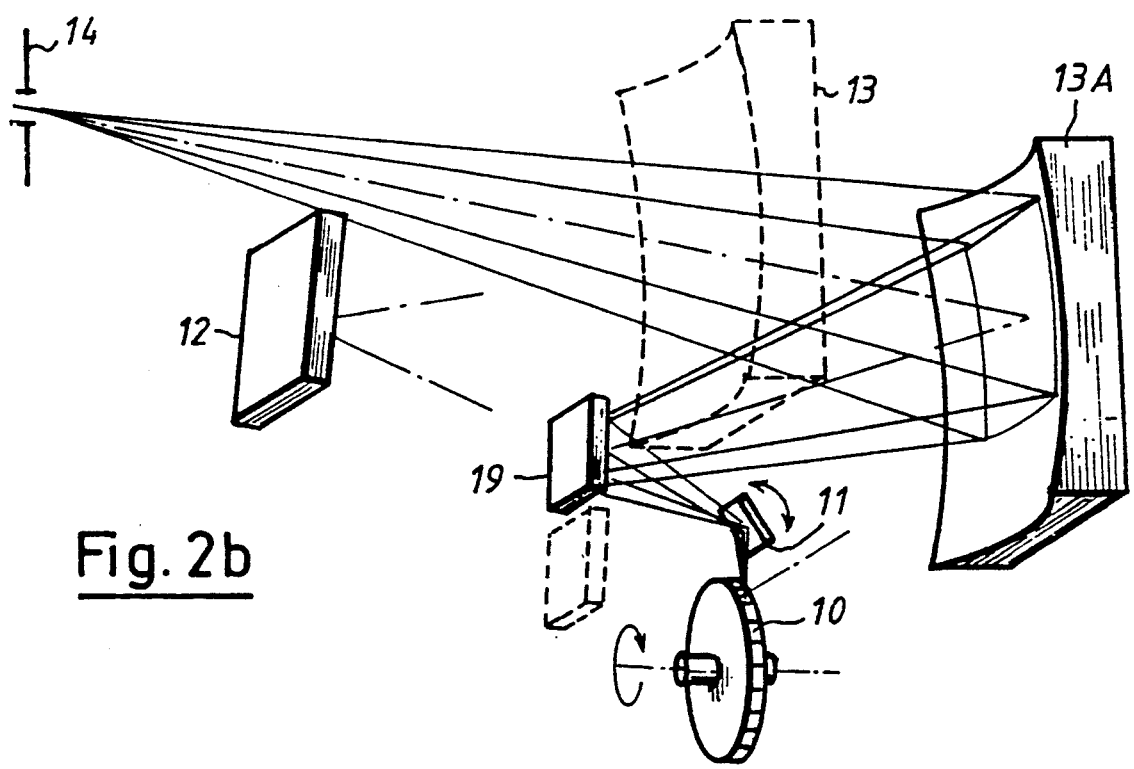
FIG. 2b corresponds to FIG. 2a except that the concave mirror is in a second switching position; and, FIG. 3 is a schematic of the displacing mechanism.

The components in FIGS. 2a and 2b which are the same as in FIGS. 1 and 3 are provided with the same reference numerals. The concave mirror 13 in FIG. 2a is switched into the first position. The switching mirror 19 is than switched out of the beam path. In this switching position, the scanning unit is imaged on the pupil 14 with a magnification scale of $\sqrt{2}$.

In FIG. 2b, the concave mirror 13A is switched into the second switching position. The deflecting mirror 19 is now switched into the beam path. In this switching position, the scanning unit is imaged on the pupil 14 at a magnification scale of $1/\sqrt{2}$ onto the pupil 14. Referring to FIG. 2a, the light beams are deflected about the axis M. As shown in FIG. 2a, the axis M intersects the mirror (13, 13A) at different locations in both switching positions. The astigmatic focus difference is the same in the two switching positions because of this displacement of the spherical mirror perpendicular to its main axis.

It is understood that the foregoing description is that of the preferred embodiments of the invention and that various changes and modifications may be made thereto without departing from the spirit and scope of the invention as defined in the appended claims.

What is claimed is:

1. An ophthalmoscope defining an optical beam path, said ophthalmoscope comprising:

a light source for transmitting a light beam along said beam path;

scanning means for deflecting the light of said light source;

a spherical concave mirror defining a main axis and imaging said scanning means onto the eye of a patient; and, shifting means for shifting said concave mirror between a first position wherein said main axis extends along a first line and said concave mirror is separated from said scanning means by a first optical path distance and a second position wherein said main axis extends along a second line parallel to said first line and said concave mirror is separated from said scanning means by a second optical path distance less than said first optical path distance so as to cause said scanning means to be imaged on the eye of the patient with first and second imaging scales when said concave mirror is in said first and second positions, respectively.

2. The ophthalmoscope of claim 1, said first and second lines being separated a distance not equal to zero.

3. The ophthalmoscope of claim 2, said scanning means including a first scanner for scanning the eye in a first scanning direction and a second scanner for scanning the eye in a second scanning direction perpendicular to said first scanning direction; and, said first and second scanners being mutually separated by a fixed spacing measured along said beam path.

4. The ophthalmoscope of claim 3, said scanners being sharply imaged on the eye of the patient simultaneously.

5. The ophthalmoscope of claim 4, one of said scanners being a polygon-mirror scanner.

6. The ophthalmoscope of claim 3, said concave mirror having a sagittal focus and a tangential focus; and, said first and second scanners being mounted in said sagittal focus and said tangential focus, respectively, whereby said scanners are focused sharply in the plane of the pupil of the eye of the patient.

7. The ophthalmoscope of claim 6, said first scanner being a polygon-mirror scanner and said second scanner being a galvanometer scanner.

8. The ophthalmoscope of claim 1, said shifting means including a linear translation device for linearly translating said concave mirror between said first and second positions with the translation being effected with a component of displacement perpendicular to said main axis.

9. The ophthalmoscope of claim 8, said linear translation device including two guide elements and said concave mirror being displaceably mounted on said guide elements so as to be displaceable between said positions.

10. The ophthalmoscope of claim 8, further comprising electric-motor driven drive means for driving said linear translation device.

11. The ophthalmoscope of claim 1, further comprising a deflecting mirror displaceable into the beam path between said scanning means and said concave mirror.

12. The ophthalmoscope of claim 1, wherein at least a portion of said optical beam path is a common illuminating and viewing optical beam path and wherein said ophthalmoscope further comprises:

said light source being configured to be a point light source defining a plane;

said scanning means being mounted in said common illuminating and viewing optical beam path for scanning the ocular fundus of the eye with the light of said point light source whereupon back-reflected light is produced which travels back along said optical beam path;

optical means defining a viewing optical beam path separate from said common illuminating and viewing optical beam path;

transmittent-deflective means arranged in said common illuminating and viewing optical beam path for deflecting said back-reflected light out of said common illuminating and viewing optical beam path into said viewing optical beam path;

a pinhole diaphragm mounted in said viewing optical beam path and defining a plane confocal to said plane of said light source; and, a detector mounted downstream of said pinhole diaphragm for detecting said back-reflected light.

13. The ophthalmoscope of claim 12, further comprising compensation means mounted in said common illuminating and viewing optical beam path for compensating for the ametropia of the eye of the patient.

14. The ophthalmoscope of claim 13, further comprising first and second apparatus parts movable relative to each other;
   said point light source, said scanning means, said concave mirror and said pinhole diaphragm all being mounted in said first apparatus part;
   said detector being mounted in said second apparatus part; and,
   said ophthalmoscope further including a flexible light-conducting fiber for transmitting said back-reflected light from said pinhole diaphragm to said detector.

15. An ophthalmoscope defining an optical beam path, said ophthalmoscope comprising:
   a light source for transmitting a light beam along said beam path;
   scanning means for deflecting the light of said light source;
   a spherical concave mirror defining a main axis and reflecting said scanning means onto the eye of a patient;
   shifting means for shifting said concave mirror between a first position wherein said main axis extends along a first line and said concave mirror is separated from said scanning means by a first optical path distance and a second position wherein said main axis extends along a second line parallel to said first line and said concave mirror is separated from said scanning means by a second optical path distance less than said first optical path distance; and,
   said shifting means including a linear translation device for linearly translating said concave mirror between said first and second positions with the translation being effected with a component of displacement perpendicular to said main axis.

16. The ophthalmoscope of claim 15, said linear translation device including two guide elements and said concave mirror being displaceably mounted on said guide elements so as to be displaceable between said positions.

17. The ophthalmoscope of claim 15, further comprising electric-motor driven drive means for driving said linear translation device.

18. An ophthalmoscope defining an optical beam path, said ophthalmoscope comprising:
   a light source for transmitting a light beam along said beam path;
   scanning means for deflecting the light of said light source;
   a spherical concave mirror defining a main axis and reflecting said scanning means onto the eye of a patient;
   shifting means for shifting said concave mirror between a first position wherein said main axis extends along a first line and said concave mirror is separated from said scanning means by a first optical path distance and a second position wherein said main axis extends along a second line parallel to said first line and said concave mirror is separated from said scanning means by a second optical path distance less than said first optical path distance;
   said scanning means including a first scanner for scanning the eye in a first scanning direction and a second scanner for scanning the eye in a second scanning direction perpendicular to said first scanning direction; and, said first and second scanners being mutually separated by a fixed spacing measured along said beam path; and,
   said concave mirror having a sagittal focus and a tangential focus; and, said first and second scanners being mounted in said sagittal focus and said tangential focus, respectively, whereby said scanners are focused sharply in the plane of the pupil of the eye of the patient.

19. The ophthalmoscope of claim 18, further comprising a deflecting mirror displaceable into the beam path between said scanning means and said concave mirror.

20. The ophthalmoscope of claim 18, wherein at least a portion of said optical beam path is a common illuminating and viewing optical beam path and wherein said ophthalmoscope further comprises:
   said light source being configured to be a point light source defining a plane;
   said scanning means being mounted in said common illuminating and viewing optical beam path for scanning the ocular fundus of the eye with the light of said point light source whereupon back-reflected light is produced which travels back along said optical beam path;
   optical means defining a viewing optical beam path separate from said common illuminating and viewing optical beam path;
   transmittent-deflective means arranged in said common illuminating and viewing optical beam path for deflecting said back-reflected light out of said common illuminating and viewing optical beam path into said viewing optical beam path;
   a pinhole diaphragm mounted in said viewing optical beam path and defining a plane confocal to said plane of said light source; and,
   a detector mounted downstream of said pinhole diaphragm for detecting said back-reflected light.

21. The ophthalmoscope of claim 18, said first scanner being a polygon-mirror scanner and said second scanner being a galvanometer scanner.

* * * * *